US006083514A

United States Patent [19]

Chang et al.

[11] Patent Number: 6,083,514

[45] Date of Patent: Jul. 4, 2000

[54] POLYMETHYLPENTENE CONTAINER FOR AN INHALATION ANESTHETIC

[75] Inventors: Steve H. Chang, Gurnee; Keith R. Cromack, Lake Bluff; Mary Jane Flament-Garcia, Gurnee; Joan Garapolo, Libertyville; David Loffredo, Elmhurst; Rajagopalan Raghavan, Grayslake; George M. Ramsay; Patrick Rice, both of Waukegan; Jeffrey Setesak, Lincolnshire, all of Ill.

[73] Assignee: Abbott Laboratories, Abbott Park, Ill.

[21] Appl. No.: 09/004,792

[22] Filed: Jan. 9, 1998

[51] Int. Cl.[7] .......... A61K 9/48

[52] U.S. Cl. .......... 424/400; 424/451; 424/457; 424/464; 424/468

[58] Field of Search .......... 424/400, 451, 424/457, 464, 468

[56] References Cited

U.S. PATENT DOCUMENTS

| | | | |
|---|---|---|---|
| 4,564,363 | 1/1986 | Bagnall et al. | 604/891 |
| 5,114,715 | 5/1992 | Young et al. | 424/400 |
| 5,391,579 | 2/1995 | Baker et al. | 514/722 |
| 5,505,236 | 4/1996 | Grabenkort et al. | 141/329 |

*Primary Examiner*—Jose' G. Dees
*Assistant Examiner*—Kathryne E. Shelborne
*Attorney, Agent, or Firm*—Brian R. Woodworth

[57] ABSTRACT

A pharmaceutical product. The pharmaceutical product includes a container constructed from a material containing polymethylpentene. The container defines an interior space. A volume of a fluoroether-containing inhalation anesthetic is contained in the interior space defined by the container.

12 Claims, 1 Drawing Sheet

POLYMETHYLPENTENE CONTAINER FOR AN INHALATION ANESTHETIC

BACKGROUND OF THE INVENTION

The present invention relates to a container for an inhalation anesthetic and a method for storing an inhalation anesthetic. In particular, the present invention is directed to a container constructed from a polymethylpentene material that provides a barrier to vapor transmission through a wall of the container and that is non-reactive with an inhalation anesthetic contained therein.

Fluoroether inhalation anesthetic agents such as sevoflurane (fluoromethyl-2,2,2-trifluoro-1-(tri fluoromethyl)ethyl ether), enflurane (2-chloro-1,1,2-trifluoroethyl difluoromethyl ether), isoflurane (1-chloro-2,2,2-trifluoroethyl difluoromethyl ether), methoxyflurane (2,2-dichloro-1,1-difluoroethyl methyl ether) and desflurane (2-difluoromethyl 1,2,2,2-tetrafluoroethyl ether) are typically distributed in containers constructed of glass. Although these fluoroether agents have been shown to be excellent anesthetic agents, it has been found that under certain conditions the fluoroether agent and the glass container may interact, thereby facilitating degradation of the fluoroether agent. This interaction is believed to result from the presence of Lewis acids in the glass container material. Lewis acids have an empty orbital which can accept an unshared pair of electrons and thereby provide a potential site for reaction with the alpha fluoroether moiety (—C—O—C—F) of the fluoroether agent. Degradation of these fluoroether agents in the presence of a Lewis acid may result in the production of degradation products such as hydrofluoric acid.

The glass material currently used to contain these fluoroether agents is referred to as Type III glass. This material contains silicon dioxide, calcium hydroxide, sodium hydroxide and aluminum oxide. Type III glass provides a barrier to the transmission of vapor through the wall of the container, thereby preventing the transmission of the fluoroether agent therethrough and preventing the transmission of other vapors into the container. However, the aluminum oxide contained in glass materials such as type III glass tend to act as Lewis acids when exposed directly to the fluoroether agent, thereby facilitating degradation of the fluoroether agent. The degradation products produced by this degradation, e.g., hydrofluoric acid, may etch the interior surface of the glass container, thereby exposing additional quantities of aluminum oxide to the fluoroether compound and thereby facilitating further degradation of the fluoroether compound. In some cases, the resulting degradation products may compromise the structural integrity of the glass container.

Efforts have been made to inhibit the reactivity of glass to various chemicals. For example, it has been found that treating glass with sulfur will protect the glass material in some cases. However, it will be appreciated that the presence of sulfur on the surface of a glass container is not acceptable in many applications.

Furthermore, glass containers present a breakage concern. For example, glass containers may break when dropped or otherwise subjected to a sufficient force, either in use or during shipping and handling. Such breakage can cause medical and incidental personnel to be exposed to the contents of the glass container. In this regard, inhalation anesthetic agents evaporate quickly. Thus, if the glass container contains an inhalation anesthetic such as sevoflurane, breakage of the container may necessitate evacuation of the area immediately surrounding the broken container, e.g, an operating room or medical suite.

Efforts to address breakage concerns typically have involved coating the exterior, non-product contact surfaces of the glass with polyvinyl chloride (PVC) or synthetic thermoplastic resin such as Surlyn® (a registered trademark of E.I. Du Pont De Nemours and Company). These efforts increase the cost of the containers, are not aesthetically pleasing, and do not overcome the above-discussed problems related to degradation which can occur when using glass to contain fluoroether-containing inhalation anesthetic agents.

For these reasons, it is desirable to provide a container constructed from a material other than glass in order to store, transport, and dispense inhalation anesthetics, thereby avoiding the above-discussed shortcomings of glass. The preferred material does not contain Lewis acids which can promote the degradation of the inhalation anesthetic agent, provides a sufficient barrier to vapor transmission into and out of the container, and increases the container's resistance to breakage relative to a glass container.

SUMMARY OF THE INVENTION

The present invention is directed to a pharmaceutical product. The product includes a container constructed from a material containing polymethylpentene. The container defines an interior space in which a volume of a fluoroether-containing inhalation anesthetic is contained.

In an alternative embodiment, the present invention is directed to a pharmaceutical product in which a container defining an interior space has an interior surface adjacent to the interior space. The interior surface of the container is constructed from a material containing polymethylpentene. A volume of a fluoroether-containing inhalation anesthetic is contained in the interior space of the container.

The present invention is further directed to a method for storing an inhalation anesthetic. The method includes the step of providing a predetermined volume of a fluoroether-containing inhalation anesthetic. A container also is provided, the container being constructed from a material containing polymethylpentene. The container defines an interior space. The predetermined volume of fluoroether-containing inhalation anesthetic is placed in the interior space of the container.

In an alternative embodiment of the method of the present invention, a predetermined volume of a fluoroether-containing inhalation anesthetic is provided. In addition, a container having an interior surface defining an interior space is provided. The interior surface of the container is constructed from a material containing polymethylpentene. The predetermined volume of a fluoroether-containing inhalation anesthetic is placed in the interior space of the container.

BRIEF DESCRIPTION OF THE DRAWINGS

For a more complete understanding of the present invention, reference may be had to the following Detailed Description read in connection with the accompanying drawing in which.

DETAILED DESCRIPTION

Figure 1:
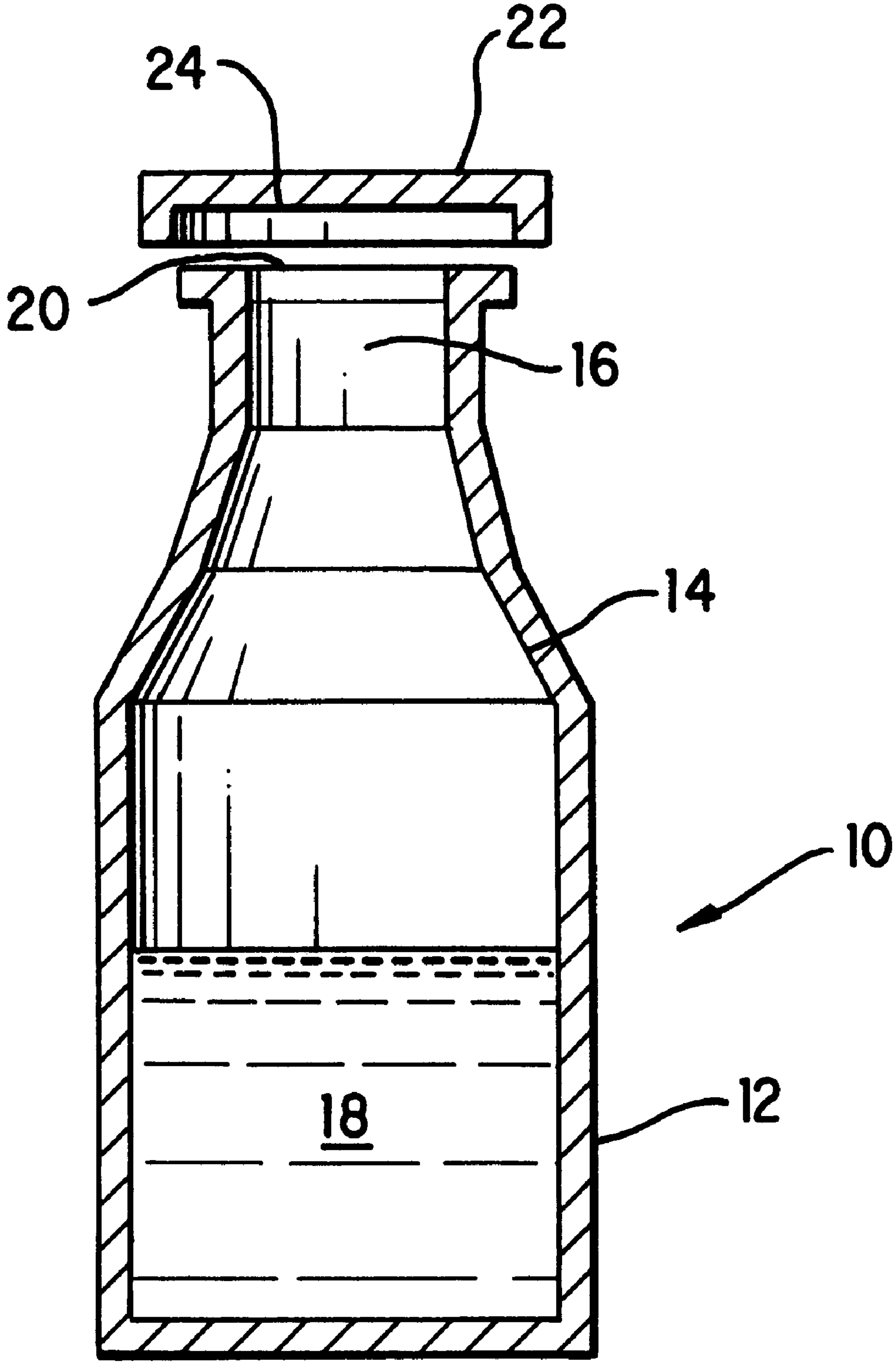
FIG. 1 is cross-sectional view of a pharmaceutical product constructed in accordance with the present invention.

A pharmaceutical product constructed in accordance with the present invention is generally indicated at 10 of FIG. 1. Pharmaceutical product 10 includes container 12 having an interior surface 14. Interior surface 14 defines an interior space 16 within container 12. An inhalation anesthetic 18 is contained within interior space 16 of container 12. In a preferred embodiment of the present invention, inhalation anesthetic 18 contains a fluoroether compound. Fluoroether-containing inhalation anesthetics useful in connection with the present invention include, but are not necessarily limited to, sevoflurane, enflurane, isoflurane, methoxyflurane, and desflurane. Inhalation anesthetic 18 is a fluid, and may include a liquid phase, a vapor phases, or both liquid and vapor phases. FIG. 1 depicts inhalation anesthetic 18 in a liquid phase.

The purpose of container 12 is to contain inhalation anesthetic 18. In the embodiment of the present invention depicted in FIG. 1, container 12 is in the shape of a bottle. However, it will be appreciated that container 12 can have a variety of configurations and volumes without departing from the spirit and scope of the present invention. For example, container 12 can be configured as a shipping vessel for large volumes (e.g., tens or hundreds of liters) of inhalation anesthetic 18. Such shipping vessels can be rectangular, spherical, or oblong in cross-section without departing from the intended scope of the invention.

Container 12 preferably is constructed of a material that minimizes the amount of vapor transmission into and out of container 12, thereby minimizing the amount of inhalation anesthetic 18 that is released from interior space 16 of container 12 and thereby minimizing the amount of vapor transmission, e.g., water vapor transmission, from an external environment of container 12 into interior space 16 and thus into inhalation anesthetic 18. Container 12 also is preferably constructed of a material that does not facilitate degradation of inhalation anesthetic 18. In addition, container 12 preferably is constructed of a material that minimizes the potential for breakage of container 12 during storage, shipping, and use.

It has been found that containers constructed from a material that contains polyethylene napthalate provide the desired vapor barrier, chemical interaction, and strength characteristics when used with inhalation anesthetics 18. One of ordinary skill will appreciate that there are many different types of polyethylene napthalate polymers which vary in their molecular weight, additives, and napthalate content. These polymers can be categorized into three distinct groups; namely, homopolymers, copolymers and blends. It has been found that polyethylene napthalate homopolymers provide higher barriers to vapor transmission when compared to copolymers and blends. For this reason, it is preferable that the material from which container 12 of the present invention is constructed contains a polyethylene napthalate homopolymer. However, it will be appreciated that certain copolymers and blends of polyethylene napthalate can be used in connection with the present invention, provided they provide an adequate barrier to the transmission of vapors, e.g., inhalation anesthetic and water vapors, therethrough, and provided that they provide the desired strength and non-reactivity to inhalation anesthetic 18.

In addition to the desirable vapor barrier characteristics of materials containing polyethylene napthalate, polyethylene napthalate does not contain Lewis acids and therefore does not pose any threat of facilitating the degradation of a fluoroether-containing inhalation anesthetic contained in a container constructed therefrom.

An example of a polyethylene napthalate material useful in connection with the present invention is HiPERTUF™ 90000 polyester resin (trademark of Shell Chemical Company), a 2,6 dimethyl napthalate based polyethylene napthalate. One of ordinary skill will appreciate that other polyethylene napthalates can be used without departing from the scope of the invention set forth in the appended claims.

In a first embodiment of the present invention, container 12 is constructed of a single layer of material. That is, container 12 is substantially homogenous throughout its thickness. In this embodiment, as above-discussed, container 12 is constructed of a material that contains polyethylene napthalate.

In an alternative embodiment of the present invention, container 12 is multi-laminar. As used herein, the term multi-laminar is intended to include (i) materials constructed of more than one lamina where at least two of the lamina are constructed of different materials, i.e., materials that are chemically or structurally different, or materials that have different performance characteristics, wherein the lamina are bonded to one another or otherwise aligned with one another so as to form a single sheet; (ii) materials having a coating of a different material; (iii) materials having a liner associated therewith, the liner being constructed of a different material; and (iv) known variations of any of the above. In this alternative embodiment of the present invention, interior surface 14 of container 12 is preferably constructed of a material containing polyethylene napthalate. It will be appreciated that the surface of container 14 in contact with a fluoroether-containing inhalation anesthetic contained therein will preferably contain polyethylene napthalate in order to provide the desired vapor barrier characteristics and simultaneously minimize the likelihood of degradation of the fluoroether-containing inhalation anesthetic.

In an alternative embodiment of the present invention, container 12 is constructed of a material containing polymethylpentene. In a preferred embodiment, a polycyclomethylpentene is used. An example of a polymethylpentene material useful in connection with the present invention is "Daikyo Resin CZ" which is manufactured and distributed by the Daikyo/Pharma-Gummi/West Group. This is a polycyclomethylpentene material. In another alternative embodiment of the present invention, interior surface 14 of container 12 is constructed of a material containing polymethylpentene.

As depicted in FIG. 1, container 12 defines an opening 20. Opening 20 facilitates the filling of container 12 and provides access to the contents of container 12, thereby allowing the contents to be removed from container 12 when they are needed. In the embodiment of the present invention depicted in FIG. 1, opening 20 is a mouth of a bottle. However, it will be appreciated that opening 20 can have a variety of known configurations without departing from the scope of the present invention.

Cap 22 is constructed to seal fluidly opening 20, thereby fluidly sealing inhalation anesthetic 16 within container 12. Cap 22 can be constructed of a variety of known materials. However, it is preferable that cap 22 be constructed of a material that minimizes the transmission of vapor therethrough and that minimizes the likelihood of degradation of inhalation anesthetic 16. In a preferred embodiment of the present invention, cap 22 is constructed from a material containing polyethylene napthalate. In an alternative embodiment of the present invention, cap 22 has an interior surface 24 that is constructed from a material containing polyethylene napthalate. In another alternative embodiment of the present invention, cap 22, and/or interior surface 24 thereof, is constructed of a material containing polyethylene, the material having vapor barrier characteristics sufficient to minimize the transmission of water vapor and inhalation anesthetic vapor therethrough. In still another alternative embodiment of the present invention, cap 22, and/or interior surface 24 thereof, is constructed of a material containing polymethylpentene.

Cap 22 and container 12 can be constructed such that cap 22 can be threadingly secured thereto. Containers and caps of this type are well known. Alternative embodiments of cap 22 and container 12 are also possible and will be immediately recognized by those of ordinary skill in the relevant art. Such alternative embodiments include, but are not necessarily limited to, caps that can be "snap-fit" on containers, caps that can be adhesively secured to containers, and caps that can be secured to containers using known mechanical devices, e.g., a ferrule. In the preferred embodiment of the present invention, cap 22 and container 12 are configured such that cap 22 can be removed from container 12 without causing permanent damage to either cap 22 or container 12, thereby allowing a user to reseal opening 20 with cap 22 after the desired volume of inhalation anesthetic 18 has been removed form container 12.

Container 12 may include additional features that form no part of the present invention. For example, container 12 can be configured to include a system for dispensing inhalation anesthetic 18 from container 12 into an anesthesia vaporizer. U.S. Pat. No. 5,505,236 to Grabenkort discloses such a system.

Methods for making containers of the type used in the present invention are known in the art. For example, it is known that polyethylene napthalate must be dried to a moisture level of approximately 0.005% prior to processing in order to yield the optimal physical properties in container 12 and cap 22. A preferred method for making containers 12 and caps 22 useful in connection with the present invention entails the injection-stretch-blow molding of a material containing polyethylene napthalate. Machines manufactured by AOKI Technical Laboratory, Inc. of Tokyo, Japan are particularly useful in performing this molding operation. The polyethylene napthalate-containing material is injection molded into a preform which is then transferred to a blow station where it is stretched and blown to form the container. The container is then batch heated and annealed in a convective oven.

It has been found that annealing of a material containing polyethylene napthalate increases the degree of crystallization in the material to a level not attainable using a blow molding process alone. Increased crystallization results in a higher barrier to vapor transmission, thereby enhancing the vapor barrier performance characteristics of a container 12 constructed of an annealed material containing polyethylene napthalate. Increased crystallization also reduces the overall weight of container 12 (based upon the weight required to attain a selected container strength) and the amount of material required to achieve a given container strength for container 12. Increased container strength allows a container to withstand greater loads during shipping, storage, and use, thereby minimizing breakage of the container. For example, greater container strength is desirable when containers 12 are placed one on top of another, as can occur when containers 12, or cartons or pallets of containers 12, are stacked for shipping or storage. It should be noted that a container constructed of a material containing an annealed polyethylene napthalate weighs less than a glass container having comparable strength characteristics, is less susceptible to breakage than a glass container of comparable weight, and costs less to manufacture than a glass container of comparable performance characteristics. A lower container weight also reduces the costs associated with shipping such containers. Further, such a container does not present the potential for degradation of a fluoroether-containing inhalation anesthetic that is present with a glass container.

The method of the present invention includes the step of providing a predetermined volume of a fluoroether-containing inhalation anesthetic 16. The fluoroether-containing inhalation anesthetic 16 can be one or more of sevoflurane, enflurane, isoflurane, methoxyflurane, and desflurane. A container 12 constructed in accordance with the above-described pharmaceutical product also is provided. In particular, container 12 defines an interior space and is constructed of a material containing polyethylene napthalate. The method of the present invention further includes the step of placing the predetermined volume of fluoroether-containing inhalation anesthetic 16 into the interior space defined by the container.

In an alternative embodiment of the method of the present invention, a predetermined volume of a fluoroether-containing inhalation anesthetic 16 is provided. The fluoroether-containing inhalation anesthetic 16 can be one or more of sevoflurane, enflurane, isoflurane, methoxyflurane, and desflurane. A container 12 constructed in accordance with the above-described product also is provided. In particular, container 12 has an interior surface 14 which defines an interior space 16. Interior surface 14 of container 12 is constructed of a material containing polyethylene napthalate. The method further includes the step of placing the predetermined volume of fluoroether-containing inhalation anesthetic into the interior space defined by the container.

In another alternative embodiment of the method of the present invention, a predetermined volume of a fluoroether-containing inhalation anesthetic 16 is provided. The fluoroether-containing inhalation anesthetic 16 can be one or more of sevoflurane, enflurane, isoflurane, methoxyflurane, and desflurane. A container 12 constructed in accordance with the above-described product also is provided. In particular, container 12 defines an interior space and is constructed of a material containing polymethylpentene. The method further includes the step of placing the predetermined volume of a fluoroether-containing inhalation anesthetic 16 into the interior space defined by the container.

In yet another alternative embodiment of the method of the present invention, a predetermined volume of a fluoroether-containing inhalation anesthetic 16 is provided. The fluoroether-containing inhalation anesthetic 16 can be one or more of sevoflurane, enflurane, isoflurane, methoxyflurane, and desflurane. A container 12 constructed in accordance with the above-described product also is provided. In particular, container 12 has an interior surface 14 which defines an interior space 16. Interior surface 14 of container 12 is constructed of a material containing polymethylpentene. The method further includes the step of placing the predetermined volume of fluoroether-containing inhalation anesthetic into the interior space defined by the container.

In each of the embodiments of the method of the present invention, container 12 can define an opening 20 therein whereby opening 20 provides fluid communication between interior space 16 of container 12 and an external environment of container 12. Each of the embodiments of the present invention may further include the step of providing a cap 22 constructed of a material containing polyethylene, polyethylene napthalate, and polymethylpentene. In the alternative, cap 22 can be constructed such that an interior surface 24 thereof is constructed of a material containing polyethylene, polyethylene napthalate, and polymethylpentene. The method of the present invention further includes the step of sealing the opening defined by container 12 with cap 22.

Although the pharmaceutical product and the method of the present invention have been described herein with respect to certain preferred embodiments, it will be apparent to one of ordinary skill in the art that various modifications can be made to the invention without departing from the spirit and scope of the invention disclosed herein as claimed in the appended claims.

What is claimed is:

1. An inhalation anesthetic product comprising:

a container constructed from a material comprising polymethylpentene, said container defining an interior space constructed to contain therein, external to a patient's body, an inhalation anesthetic; and a volume of sevoflurane contained in said interior space defined by said container.

2. An inhalation anesthetic product in accordance with claim 1, wherein said container defines an opening therein, said opening providing fluid communication between said interior space defined by said container and an external environment of said container, said inhalation anesthetic product further comprising a cap, said cap constructed to seal said opening defined in said container, said cap constructed from a material comprising a compound selected from a group consisting of polyethylene, polyethylene napthalate and polymethylpentene.

3. An inhalation anesthetic product in accordance with claim 1, wherein said container defines an opening therein, said opening providing fluid communication between said interior space defined by said container and an external environment of said container, said inhalation anesthetic product further comprising a cap having an interior surface, said cap constructed to seal said opening defined in said container, said interior surface of said cap constructed from a material comprising a compound selected from a group consisting of polyethylene, polyethylene napthalate and polymethylpentene.

4. An inhalation anesthetic product comprising:

a container defining an interior space constructed to contain therein, external to a patient's body, an inhalation anesthetic, said container having an interior surface adjacent to said interior space, said interior surface constructed from a material comprising polymethylpentene; and a volume of sevoflurane contained in said container.

5. An inhalation anesthetic product in accordance with claim 4, wherein said container defines an opening therein, said opening providing fluid communication between said interior space defined by said container and an external environment of said container, said inhalation anesthetic product further comprising a cap, said cap constructed to seal said opening defined in said container, said cap constructed from a material comprising a compound selected from a group consisting of polyethylene, polyethylene napthalate and polymethylpentene.

6. An inhalation anesthetic product in accordance with claim 4 wherein said container defines an opening therein, said opening providing fluid communication between said interior space defined by said container and an external environment of said container, said inhalation anesthetic product further comprising a cap having an interior surface, said cap constructed to seal said opening defined in said container, said interior surface of said cap constructed from a material comprising a compound selected from a group consisting of polyethylene, polyethylene napthalate and polymethylpentene.

7. A method for storing an inhalation anesthetic external to a patient's body, said method comprising the steps of:

providing a predetermined volume of sevoflurane;

providing a container defining an interior space, said container constructed from a material comprising polymethylpentene; and placing said predetermined volume of sevoflurane in said interior space defined by said container.

8. A method for storing an inhalation anesthetic in accordance with claim 7, wherein said container defines an opening therein, said opening providing fluid communication between said interior space defined by said container and an external environment of said container, said method further comprising the steps of:

providing a cap constructed to seal said opening defined in said container, said cap comprising a compound selected from a group consisting of polyethylene, polyethylene napthalate and polymethylpentene; and sealing said opening defined in said container with said cap.

9. A method for storing an inhalation anesthetic in accordance with claim 7, wherein said container defines an opening therein, said opening providing fluid communication between said interior space defined by said container and an external environment of said container, said method further comprising the steps of:

providing a cap constructed to seal said opening defined in said container, said cap having an interior surface constructed from a material comprising a compound selected from a group consisting of polyethylene, polyethylene napthalate and polymethylpentene; and sealing said opening defined in said container with said cap.

10. A method for storing an inhalation anesthetic external to a patient's body, said method comprising the steps of:

providing a predetermined volume of sevoflurane;

providing a container defining an interior space, said container having an interior wall adjacent said interior space defined by said container, said interior wall of said container constructed from a material comprising polymethylpentene; and placing said predetermined volume of sevoflurane in said interior space defined by said container.

11. A method for storing an inhalation anesthetic in accordance with claim 10, wherein said container defines an opening therein, said opening providing fluid communication between said interior space defined by said container and an external environment of said container, said method further comprising the steps of:

providing a cap constructed to seal said opening defined in said container, said cap comprising a compound selected from a group consisting of polyethylene, polyethylene napthalate and polymethylpentene; and sealing said opening defined in said container with said cap.

12. A method for storing an inhalation anesthetic in accordance with claim 10, wherein said container defines an opening therein, said opening providing fluid communication between said interior space defined by said container and an external environment of said container, said method further comprising the steps of:

providing a cap constructed to seal said opening defined in said container, said cap having an interior surface constructed from a material comprising a compound selected from a group consisting of polyethylene, polyethylene napthalate and polymethylpentene; and sealing said opening defined in said container with said cap.

* * * * *